United States Patent [19]

Grimsrud

[11] 4,061,031
[45] Dec. 6, 1977

[54] COMBINATION OF FLOW METER AND BUBBLE TRAP

[76] Inventor: Lars Grimsrud, P.O. Box 1379, Salmon, Idaho 83467

[21] Appl. No.: 628,971

[22] Filed: Nov. 5, 1975

[51] Int. Cl.$^2$ .................. A61B 5/02; A61M 1/03; G01F 1/20; G01F 15/08

[52] U.S. Cl. ................. 73/200; 23/258.5 R; 23/258.5 B; 23/258.5 M; 73/215; 55/36; 55/159; 55/178; 128/2.05 F; 210/188

[58] Field of Search .......... 23/258.5 R, 258.5 A, 23/258.5 B, 258.5 BH, 258.5 M, 258.5 MH; 210/87, 88, 89, 188, 22, 321 K; 128/214 R, 214 C, 2.05 F, 214.2; 137/171, 202; 73/200, 215, 216; 55/18, 36, 270, 178, 159

[56] References Cited

U.S. PATENT DOCUMENTS

| | | | |
|---|---|---|---|
| 1,505,050 | 8/1924 | Lauritsen | 73/215 |
| 2,292,007 | 8/1942 | Morgan | 73/200 X |
| 3,044,236 | 7/1962 | Bearden et al. | 55/270 X |
| 3,527,572 | 9/1970 | Urkiewicz | 23/258.5 B |
| 3,769,207 | 10/1973 | Baer | 55/178 X |

FOREIGN PATENT DOCUMENTS

| | | | |
|---|---|---|---|
| 1,806,654 | 5/1970 | Germany | 73/215 |
| 296,007 | 1/1954 | Switzerland | 210/63 |

*Primary Examiner*—Morris O. Wolk
*Assistant Examiner*—Michael S. Marcus
*Attorney, Agent, or Firm*—Watson, Cole, Grindle & Watson

[57] ABSTRACT

Combination of a flow meter and a bubble trap for blood which has been extracted for extra-corporeal treatment, in particular for dialysis. Said combination comprises a container divided by a vertical partition wall into a vertically elongated inlet chamber having an inlet opening receiving the blood flow to be measured and treated, and an outlet chamber of substantially greater cross-section than the inlet chamber and in liquid communication with an outlet opening. According to the invention, a narrow passage with a substantially smaller cross-section than the inlet opening is provided through the partition wall, preferably near the lower end of the same, causing the liquid level in the elongated inlet chamber to rise substantially above the level of said narrow passage. The difference between the liquid levels in the respective chambers will be an indication of the blood flow rate through the container, a pressure equalization opening being provided through the wall above said liquid levels. Both chambers are serving as efficient bubble traps, the influx of blood to the inlet chamber taking place below the liquid level and preferably in a vertical direction, and the output chamber providing the advantageous combination of an extended free surface and a reduced blood flow rate.

7 Claims, 1 Drawing Figure

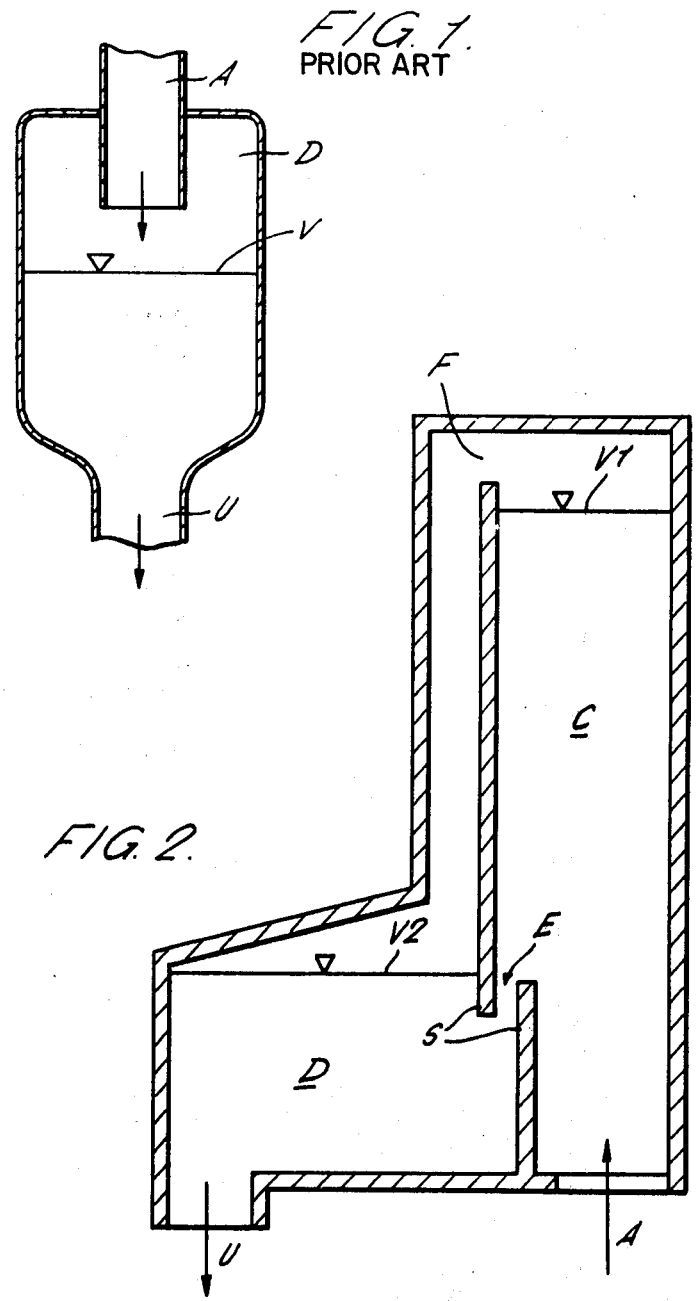

COMBINATION OF FLOW METER AND BUBBLE TRAP

The present invention concerns a combination of a flow meter and a bubble trap for blood which has been extracted for extracorporeal treatment, in particular for dialysis.

When performing such extra-corporeal treatment, for example, dialysis of blood from patients with kidney diseases, monitoring the flow of blood through the external circuit is very important. The usual and simplest method for measuring this flow of blood consists in timing the transit of an air bubble from one permanent mark to another on a transparent tubing. Better blood and more accurate flow meters have, of course, also been developed, but their use with routine treatments is too costly, due to the large number of patients being treated simultaneously, and due to the requirement for technically competent personnel to operate such flow meters properly.

The extra-corporeal blood flow circuit should also contain one or more bubble traps for removing air bubbles from the blood, since it is well known that such bubbles may be detrimental and even lethal to the patient, if they are allowed to enter his circulatory system. Bubble traps employed at the present time for this purpose are designed according to the principle shown in FIG. 1 of the accompanying drawing.

As shown by an arrow in FIG. 1, the blood is introduced through an inlet tube A to a chamber D, which is only partially filled with blood, the inlet tube A opening in the air above the liquid level V in chamber D. As equally shown by an arrow in the Figure, the blood leaves the bubble trap through an outlet U for a further circulation through the extra-corporeal circuit.

Bubble traps of the above design appear, however, in practice often to behave more like bubble generators than bubble traps, since a heavy flow of blood tends to whisk additional air into the blood, and this newly entrapped air is unlikely to rise into the air pocket above the surface V due to the small cross-section of the trap and the concomitant downwardly directed rapid blood flow velocity.

On this background, it is an object of the present invention to provide a simple and inexpensive combination of a flow meter and a bubble trap for blood, allowing both a more easily determined flow reading than the commonly utilised flow meters and overcoming the above-noted disadvantages of known bubble traps. This combination comprises a container through which the blood flows between an inlet opening and an outlet opening, said container being, according to the present invention, vertically divided into two chambers by means of a partition wall, namely an inlet chamber in communication with the inlet opening and an outlet chamber in communication with the outlet opening. A narrow flow passage of substantially smaller cross-section than the inlet opening is provided between said chambers through the partition wall, preferably near its lower end, and said wall has an opening above the liquid levels of the respective chambers for air pressure equalization.

Since said narrow passage between the chambers is of substantially smaller cross-section than the inlet opening, the liquid level in the inlet chamber rises substantially above the level of the narrow passage. The difference between liquid levels in the respective chambers is thus an indication of the blood flow through the narrow passage, which is identical to the blood flow in all parts of the extra-corporeal circuit.

Due to said pressure equalization opening, the air pressure in the chambers is equal. Said difference between liquid levels in the chambers is then approximately proportional to the square of the liquid flow rate in the circuit. According to the invention, the outlet chamber is preferably designed with a substantially larger horizontal cross-section than the inlet chamber, which means that the liquid level in the outlet chamber changes much less than the liquid level in the inlet chamber with blood flow variations. Such variations in the blood flow may then easily be monitored by keeping an eye on the liquid level in the inlet chamber only, and ignoring the small variations of the liquid level in the outlet chamber.

The present invention will now be described by way of an example of an embodiment, with reference to the accompanying drawings, wherein:

FIG. 1 is a schematic diagram of a common design of a known bubble trap, and

FIG. 2 shows a vertical cross-section through a combination of a flow meter and a bubble trap according to the present invention.

FIG. 1 has been described in the preamble of the present specification and will not be the subject of further explanation. Corresponding parts in FIGS. 1 and 2 have been given identical designations.

FIG. 2 shows a vertical cross-section through a container, which, by means of a partition wall S, has been divided vertically into two chambers, namely an inlet chamber C and an outlet chamber D. The inlet chamber C is in communication with an inlet opening A at the bottom of the container, as indicated by an inwardly directed arrow, while the outlet chamber D is in communication with an outlet opening U, also at the bottom of the container and indicated by an arrow.

FIG. 2 also shows a narrow passage E with considerably smaller cross-section than the inlet opening A, allowing for blood flow through the wall S near its lower end. Near the upper end of the wall an opening F is provided for air pressure equalization between the chambers.

In operation, the present combination is connected in series with an extra corporeal blood treatment circuit, which, e.g., may contain a dialysis apparatus. The blood flowing in this circuit then flows through the inlet opening A and into chamber C. Since the passage E has a considerably smaller cross-section than the inlet A, the liquid level V1 in the inlet chamber rises to a certain level above the passage E to provide the extra pressure required for forcing the blood through the narrow passage E.

Having passed through the passage E, the blood enters the outlet chamber D which has a substantially larger cross-section than the inlet chamber C. Finally the blood leaves the container through the outlet opening U for further circulation through the rest of the extra-corporeal circuit. The difference between the liquid levels V1 and V2 is then an indication of the liquid flow rate the passage E which is identical to the flow rate everywhere in the extra-corporeal circuit. Since the cross-section of the outlet chamber D is substantially larger than that of the inlet chamber C, the level V2 changes only slightly as the flow rate varies. This means that the blood flow rate for all practical purposes is indicated by the level V1. The outer wall of the inlet chamber C may conveniently be designed with an elongated transparent window, graduated for easy reading of the liquid level V1 and thus the blood flow rate at all times.

The embodiment shown in FIG. 2, furthermore, serves as a bubble trap in a much more efficient manner than the known design of FIG. 1. As indicated in FIG. 2, the blood is introduced into the inlet chamber C below the blood level V1 in the chamber which means that the influx of blood will not in any way whisk the blood to absorb additional air bubbles. FIG. 2 shows, furthermore, that the blood is introduced into chamber C in an upward direction as indicated by the arrow in the inlet opening which coincides with the ascent of any possible air bubbles trapped in the new blood. Practically all entrapped air bubbles escape from the blood already in the chamber C, and any possible remaining bubbles have an excellent opportunity to escape through the surface V2 in chamber D due to the large cross-section and concomitant small flow rate in this chamber.

The combination flow meter and bubble trap of the present invention may be manufactured as a very compact unit, e.g., cast from a plastic material, and at small expense. Thus, it may be feasible to combine the device of this invention with the tubing of the extra-corporeal flow circuit to provide an inexpensive unit which may be discarded after use to save costly sterilization.

I claim:

1. An apparatus for measuring the flow rate of and for releasing entrapped air bubbles in a blood stream which has been extracted temporarily from a patient for extra-corporeal treatment comprising
   a closed container having an inlet opening and an outlet opening therein so that the blood stream can flow therethrough,
   a vertically disposed partition means for dividing the container into two chambers, respective ones of which are in direct communication with each of the openings to thereby form inlet and outlet chambers,
   first opening means in said partition means above the level of said inlet opening and said outlet opening, said first opening means being of a smaller cross-section than the inlet opening so that blood accumulates in said inlet chamber to a depth at which said first opening is sufficiently below the surface of the blood in the inlet chamber that increased pressure equalizes the blood flow rate through said first opening means thereby controlling the flow of the blood stream therethrough from said inlet chamber to said outlet chamber so that the height of blood in said inlet chamber is a function of the blood flow rate, and
   second opening means in said partition means adjacent the top thereof for equalizing the air pressure in said closed container between said inlet and outlet chambers.

2. An apparatus according to claim 1, wherein said first opening means directs the blood stream down from said inlet chamber to said outlet chamber.

3. An apparatus according to claim 1, wherein the horizontal cross-sectional area of the outlet chamber is larger than the horizontal cross-sectional area of the inlet chamber.

4. An apparatus according to claim 3, wherein the inlet opening is in the bottom of the container so that inflowing blood is directed vertically upwardly in the inlet chamber.

5. An apparatus according to claim 4, wherein the outlet opening is in the bottom of the container.

6. An apparatus according to claim 1, wherein said partition means comprises a top section and a bottom section horizontally spaced and vertically overlapping and said first opening means is the opening formed by the separation of said top and bottom wall sections.

7. An apparatus according to claim 6, wherein said bottom section is horizontally spaced towards said inlet opening and said top section is horizontally spaced towards said outlet opening.

* * * * *